United States Patent

Scheidges et al.

[11] Patent Number: 5,093,507
[45] Date of Patent: Mar. 3, 1992

[54] 10β,11β-BRIDGED STEROIDS

[75] Inventors: Cornelius Scheidges; Eckhard Ottow; Günter Neef; Sybille Beier; Walter Elger, all of Berlin, Fed Rep. of Germany

[73] Assignee: Schering Aktiengesellschaft, Berlin and Bergkamen, Fed. Rep. of Germany

[21] Appl. No.: 367,165

[22] Filed: Jun. 16, 1989

[30] Foreign Application Priority Data

Jun. 16, 1988 [DE] Fed. Rep. of Germany ....... 3820948

[51] Int. Cl.$^5$ ................................................ C07J 9/00
[52] U.S. Cl. .................................. 552/523; 514/178; 514/172
[58] Field of Search ...................... 514/169, 177, 172; 260/397.0; 552/503

[56] References Cited

U.S. PATENT DOCUMENTS 4,252,798  2/1981  Tindall .................................. 540/59

FOREIGN PATENT DOCUMENTS

A-0100566  2/1984  European Pat. Off. .
46502      2/1965  Japan .................................... 540/59

OTHER PUBLICATIONS

Neef et al., J. Org. Chem. 52, 4143-4146 (1987).

Primary Examiner—Jose G. Dees
Assistant Examiner—Deborah D. Carr
Attorney, Agent, or Firm—Millen, White & Zelano

[57] ABSTRACT

10β,11β-bridged steroids of Formula I

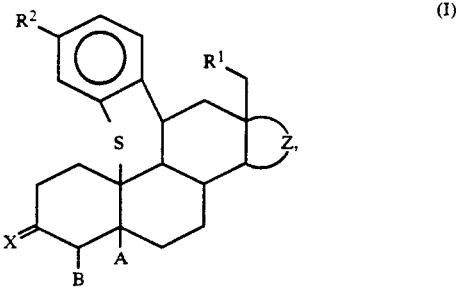

wherein
 $R^1$ is H or methyl;
 $R^2$ is H, a cyanide residue, a heteroaryl residue, a straight-chain or branched aliphatic, e.g., alkyl group of up to 20 carbon atoms, optionally exhibiting double or triple bonds and, if desired, being substituted by one or several oxo groups, a $C_{4-7}$ cycloalkyl or $C_{4-7}$ cycloalkenyl group, an $OR^3$—, $SR^3$—, —$OSO_2$—$R^{11}$— group wherein $R^{11}$ means a perfluroinated $C_1$-$C_4$-alkyl group or an $NR^3R^4$- group wherein $R^3$ means an H atom or $C_1$-$C_8$-alkyl residue, $R^4$ means $R^3$, a cyanide or a $C_1$-$C_{10}$-acyl residue, or $R^3$ and $R^4$ jointly with the inclusion of N means of 5- or 6-membered heterocyclic ring wherein the ring can additionally contain a further hetero atom N, O, or S, or a 4-cyano-, 4-methoxy- or 4-dimethylamino-substituted phenyl group,
 A and B either mean jointly a further bond between C4 and C5, or A is an α-hydroxy group and B is H,
 X is a keto or oxime group, and
 Z is a pentagonal or hexagonal ring residue which is optionally substituted and optionally unsaturated, or pharmaceutically compatible acid additional salts thereof which possess antigestagen and antiglucocorticoid properties.

25 Claims, No Drawings

$10\beta,11\beta$-BRIDGED STEROIDS

SUMMARY OF THE INVENTION

The present invention relates to $10\beta,11\beta$-bridged steroids, processes for their production, pharmaceutical preparations containing these compounds, and methods for treating various disorders utilizing these compounds, as well as the novel intermediates required therefor.

DETAILED DESCRIPTION

The $10\beta,11\beta$-bridged steroids according to this invention are described by Formula I

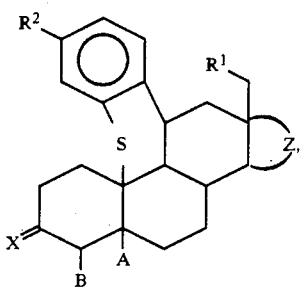

(I)

wherein $R^1$ is an H atom or a methyl group, $R^2$ is an H atom, a cyanide residue, a heteroaryl residue, a straight-chain or branched aliphatic group of up to 20 carbon atoms, for example, alkyl, optionally exhibiting double or triple bonds and, if desired, being substituted by one or several oxo groups, a $C_{4-7}$ cycloalkyl or $C_{4-7}$ cycloalkenyl group, an $OR^3$—, $SR^3$, —$OSO_2$—$R^{11}$-group wherein $R^{11}$ means a perfluorinated $C_1$-$C_4$ alkyl group or an $NR_3R_4$-group where $R^3$ means an H atom or a $C_1$-$C_8$-alkyl residue, $R^4$ means $R^3$, a cyanide or a $C_1$-$C_{10}$-acyl residue, or $R^3$ and $R^4$ jointly with the inclusion of N mean a 5- or 6-membered heterocyclic ring wherein the ring can additional contain a further hetero atom N, O or S, or a 4-cyano-, 4-methoxy- or 4-dimethylamino-substituted phenyl group, A and B either mean jointly a further bond between C4 and C5, or A stands for an $\alpha$-hydroxy group and B stands for an H atom, X is a keto or oxime group, and Z is the residue of a pentagonal or hexagonal ring which is optionally substituted and optionally unsaturated, as well as the pharmaceutically compatible acid addition salts thereof.

The number of oxo groups which may be substituted on $R^2$ when it is an aliphatic group may be up to 2.

The invention concerns, in particular, compounds of general Formula I wherein Z stands for the residue of a ring of the formula

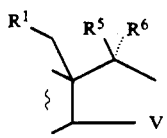

wherein $R^1$ has the meanings set forth in claim 1, the dashed line emanating from V symbolizes the possible presence of a double bond, V stands for a $CH_2$—, $CH$—, $CH_2CH_2$— or $CHCH_2$-residue and $R^5/R^6$ mean

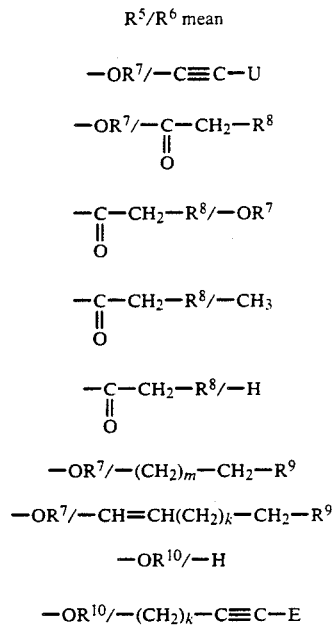

wherein E is halogen,

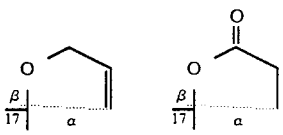

wherein $R^7$ means a hydrogen atom or acyl residue of 1-4 carbon atoms, U means a hydrogen atom, an alkyl, hydroxyalkyl, alkoxyalkyl or acyloxyalkyl group of respectively 1-4 carbon atoms in the alkyl and, respectively, acyl residue, $R^8$ means a hydrogen atom, a hydroxy group, an alkyl, O-alkyl, or O-acyl group of respectively 1-4 carbon $R^9$ means a hydrogen atom, a hydroxy or cyanide residue, an O-alkyl or O-acyl group of respectively 1-4 carbon atoms, $R^{10}$ means a hydrogen atom, an alkyl or acyl group of respectively 1-10 carbon atoms, m means 0, 1, 2 or 3, k means 0, 1 or 2.

Suitable halogens represented by E are Cl, Br, F, and I.

All alkyl groups described above and below can include methyl, ethyl, n-propyl, isopropyl, and n-, iso-, sec- and tert-butyl, and all isomers of pentyl, hexyl, heptyl, octyl, nonyl, decyl, undecyl, dodecyl, tridecyl, tetradecyl, pentadecyl, hexodecyl, heptadecyl, octadecyl, nonadecyl, and icosyl, for example.

All acyl groups described above and below can include the following alkanoyl groups: formyl, acetyl, propionyl, n-butyryl and iso-butyryl, for example. In addition, in the case of $R^3$ and $R^{10}$, acyl may also include benzoyl and substituted benzoyl.

All alkoxy groups described above and below can include methoxy, ethoxy, n-propoxy, isopropoxy, and n-, iso-, sec-, and tert-butoxy, for example.

All alkenyl groups described above and below can include ethenyl, propenyl and butenyl groups in either the E or Z configuration, for example.

Suitable heteroaryl groups have 1-2 rings, each ring having 1-3 heteroatoms, e.g., O, N or S; typically the total number of heteroatoms in the heterocycle being 1-2. Typical examples include, inter alia, 2-, 3-, and 4-pyridine, 2-, 4-, and 5-pyrimidine, pyrazine; 2- and 3-furan, 2- and 3-thiophene, and all isomers of thiazole, imidazole and indole.

Suitable heterocyclic rings will have 1-2 heteroatoms, e.g., O, N or S; the heterocycles can be aliphatic, saturated or unsaturated, or aromatic. Typical examples include, inter alia, pyrrolidine, piperidine, piperazine, indoline, imidazolidine, morpholine, pyrroline, and pyrazolidine.

The cycloalkyl and cycloalkenyl groups contained in $R^2$ may contain 4-7 carbon atoms, preferably 5 to 6 carbon atoms, e.g., cyclopentyl, cyclohexyl, cyclopentenyl, and cyclohexenyl.

The alkyl, alkoxy as well as acyloxy groups contained in $R^5$ and $R^6$ and, respectively, $R^7$, $R^8$, $R^9$, $R^{10}$ and U of general Formula I are to contain in each case 1-4 carbon atoms, the methyl, ethyl, propyl, isopropyl, methoxy, ethoxy, propoxy, isopropoxy, formyl, acetyl, and propionyl groups being preferred.

Among the alkenyl residues in $R^6$, the propenyl and butenyl groups are preferred; these can be present in the E or Z configuration. In other words, if $R^6$ stands for $-CH=CH-(CH_2)_k-CH_2-R^9$ then k is to mean preferably 0 or 1.

The novel compounds of general Formula I are prepared according to this invention by the process described below.

The starting compounds of Formula II

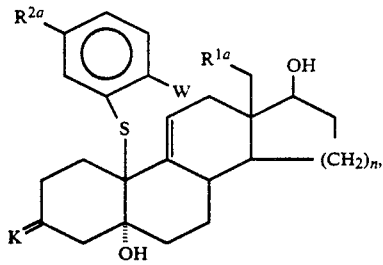
(II)

wherein $R^{1a}$ and $R^{2a}$ have the same meanings as $R^1$ and $R^2$, respectively, in general Formula I and wherein optionally hydroxy, mercapto, amino, oxo and/or terminal acetylene groups present in $R^{2a}$ are blocked, n means the number 1 or 2, K is a keto group blocked in the form of the ketal or thioketal, and W is a bromine or iodine atom, are produced, starting with the epoxides of general Formula IV obtained according to the directions in, for example, European Patent Application Publication Number 0 110 434, DE 34 38 484 or European Patent Application Publication Number 0 127 864

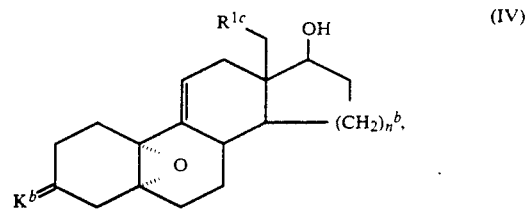

wherein $R^{1c}$, $K^b$ and $n^b$ have the same meanings as $R^1$, K and n, by nucleophilic addition of a suitable thiophenolate to the number 10 carbon atom.

Various synthesis routes can be chosen, in this connection, depending on the substituents $R^{2a}$ desired in the intermediate products.

If the thiophenolate residue to be introduced is to carry, in the m-position with respect to the sulfur atom, an amino grouping ($R^3$, $R^4=CH_3$, $C_2H_5$, as well as the corresponding monoalkyl compounds), then it is possible first to add 3-mercaptoaniline in nucleophilic fashion to the carbon atom number 10 of the steroid skeleton with the aid of a strong base, e.g. n-butyllithium, and subsequently to produce the corresponding N-monoalkyl compound by one-time acylation of the amino group and subsequent reduction of the N-monoacyl compound, or to prepare the corresponding N-dialkylamino compound by twice acylating in sucession and by reduction. Preferably, the mixed anhydride of formic acid and acetic acid is utilized as the acylating agent, and after reduction the corresponding monomethyland, respectively, dimethylamino compound is accordingly obtained. Other amino compounds according to the claims can be produced analogously.

During the acylation of the amino group, the 17-hydroxy group is in each case likewise acylated, but is then liberated again during reduction and/or during the working up of the reaction product. A preferred reducing agent utilized is a complex hydride, especially lithium aluminum hydride.

Another possibility for opening the epoxide IV resides in adding a thiophenolate of the formula

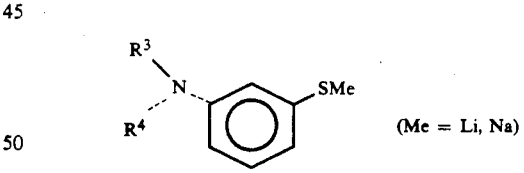
(Me = Li, Na)

to the epoxide IV in a nucleophilic fashion.

In both instances, a halogen atom (bromine or iodine) is then introduced in the o'-position of the phenyl ring by halogenation, preferably by bromination with N-bromosuccinimide. The reaction sequence set forth as the first hereinabove is demonstrated in Examples 3A to 3F for preparing 10β-(2-bromo-5-diethylaminophenylthio)-3,3-(2,2-dimethyltrimethylenedioxy)estr-9(11)-ene-5α,17β-diol.

In a further version of the process of this invention, the epoxide of Formula IV is reacted directly with a 2-bromo- or 2-iodothiophenolate already carrying in the 5-position the substituent $R^{2a}$ desired in the intermediate product of Formula II, or a precursor thereof, for example with 2-bromo-5-methoxysodium thiophenolate.

Optionally after blockage of the functional group present on the phenyl ring, the novel intermediates of Formula II are subjected to cyclizing with the formation of the 10β,11β-bridged structure.

The hydroxy, mercapto and keto blocking groups encompassed by $R^{2a}$ and K in Formula II are groups readily cleavable in an acidic medium, such as, for example, the methoxymethyl, ethoxymethyl, tetrahydropyranyl, ethylenedioxyketal, ethylenedithioketal or 2,2-dimethyltrimethylenedioxyketal group.

Blocking groups for amino and terminal acetylene groups, e.g. the trimethylsilyl and tert-butyldimethylsilyl groups, are likewise known to one skilled in the art and are split in accordance with the desired reaction sequence also by following methods known in the literature [Synthesis 1980, 627; J. Org. Chem. 46 (1986): 2280].

Cyclization of the intermediate products II to the novel 10β,11β-bridged steroids of general Formula IIIa

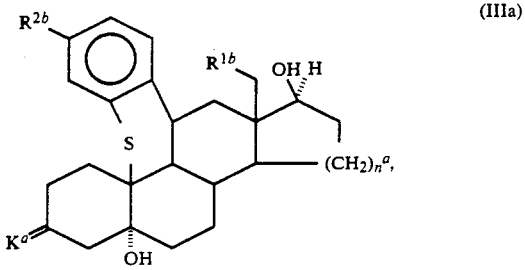

(IIIa)

wherein $R^{1b}$, $R^{2b}$, $K^a$ and $n^a$ have the same meanings as $R^1$, $R^2$, K and n, respectively, but wherein optionally a hydroxy, mercapto, amino, oxo or terminal acetylene group present in is blocked, which are likewise the subject matter of this invention, takes place by reductive radical cyclization in an inert solvent. An advantageous reducing agent in this process is, according to this invention, a trialkyltin hybride, especially tributyltin hydride, with the addition of a radical-forming agent, e.g. azobisisobutyronitrile. Toluene is an example of a suitable solvent. Cyclization is performed under reflux and, for enhancing the radical reaction, under irradiation with a light source (For example, a 300-watt bulb with tungsten filament).

Conversion of the thus-obtained cyclization products into the finally desired end products of Formula I takes place in accordance with methods know per se, in that (a) the C-17 hydroxy group is optionally oxidized and subsequently (b) if desired, a hydroxy group on the phenylene ring carrying a blocking group is freed of this blocking group, a corresponding perfluoroalkyl sulfonate is produced, if desired, from the hydroxy compound, optionally the perfluoroalkyl sulfonate is converted, with a correspondingly substituted trialkyltin compound, into a compound which, optionally after further reactions, carries on the phenylene ring the desired substitution pattern, or first (b) is performed, and then (a) is carried out, and thereafter, if desired, (c) the D ring is functionalized in the desired way according to conventional methods, the thus-obtained product is subjected, with formation of the 4(5)-double bond, to the effect of a dehydrating agent which is also capable of liberating the 3-oxo group and optionally further blocked groups, or (d) the thus-obtained product is subjected, with the formation of the 4(5)-double bond, to the effect of a dehydrating agent also capable of liberating the 3-oxo group and optionally further blocked groups, and subsequently, after blockage of the 3-oxo group, the D ring is functionalized in the desired way, or the steps (a) and (b) or (b) and (a) are executed after step (c) or (d), the thus-obtained product is optionally freed of blocking groups, the hydroxy, mercapto and/or amino group that may be present on the phenylene ring is, if desired, alkylated or acylated, if desired a cyanide residue is introduced into the phenylene ring, optionally is reacted with hydroxylamine hydrochloride to the product of Formula I wherein X means the hydroxyimino grouping N~OH, or a pharmaceutically compatible acid addition salt thereof is produced.

During the course of these reaction routes it may be necessary to intermediarily reintroduce blocking groups into intermediates, for example for functional groups contained in Z, or for the 3-keto group during the subsequent construction of the D ring.

The oxidation of the 17β-hydroxy group, required for the preparation of almost all final products, is conventionally performed, for example by Oppenauer oxidation or with chromic acid reagents (Jones reagent or chromic acid—pyridine).

In case the process of this invention is interrupted after the oxidizing step, the 17-oxidation products are obtained, derived from Formula IIIa, which are likewise the subject of the present invention.

Liberation of the 3-keto function with the simultaneous cleavage of water and formation of the 4 5)-double bond takes place by treatment with acid or an acidic ion exchanger. The acid treatment is carried out conventionally by dissolving the corresponding 5α-hydroxy-3-ketal in a water-miscible solvent, such as aqueous methanol, ethanol or acetone, and treating the solution with catalytic amounts of a mineral or sulfonic acid, such as hydrochloric acid, sulfuric acid, phosphoric acid, perchloric acid, or p-toluenesulfonic acid, or an organic acid, such as acetic acid, until the blocking group of the 3-keto function has been removed and water is split off, if desired. In this procedure, other blocking groups present can likewise be split off concomitantly in part or entirely since the acidic agent utilized for the splitting off step does not (necessarily) have a selective effect; optionally, labile groups must again be blocked after formation of the Δ4-double bond and before further reaction steps are performed. In this connection, attention is invited, as a representative example, to the reaction step 4D→4E prior to oxidation of the 17β-OH-group in Example 4F. The reaction, proceeding at temperatures of 0° to 100° C., can also be carried out with an acidic ion exchanger. The progression of the reaction can be observed by means of analytical methods, for example by subjecting withdrawn samples to thin-layer chromatography.

In general, the removal of blocking groups and the step of splitting off water is accomplished in one reaction step by allowing the corresponding 5α-hydroxy-3-ketal (or 5-ene-3-ketal) to react for a certain period of time in a strongly acidic medium. However, it is equally possible according to this invention to perform the removal of blocking groups and the step of splitting off water in two mutually separate reaction stages by first obtaining, by a shorter treatment of the corresponding 5α-hydroxy-3-ketal in a moderately acidic medium. initially the corresponding 5α-hydroxy-3-keto compound and optionally isolating same. The 5α-hydroxy-3-keto compound is then converted into the 3-keto-4-ene compound by further treatment with an acid while water is being split off.

Upon further study of the specification and appended claims, further objects and advantages of this invention will become apparent to those skilled in the art.

A quite special advantage of the present invention resides in the large bandwidth of the substituents that can be introduced at the o-phenylene ring. On the one hand, the substituent $R^2$, present in the subsequent final product, can be present already in the intermediate of Formula II by having been introduced directly with the thiophenolate via the nucleophilic addition to the epoxide of Formula IV, or by having been subsequently added at the 5-position of the added thiophenolate residue. The number of compounds producible in this way, substituted on the o-phenylene ring in the final product, is relatively limited since not all of the substituents desirable in the end product will withstand, without damage, the conditions of nucleophilic addition of the thiophenolate to the respective 5α,10α-epoxide IV and, in particular, the reductive conditions during cyclization of the intermediate product II into a 10β,11β-bridged steroid of Formula III

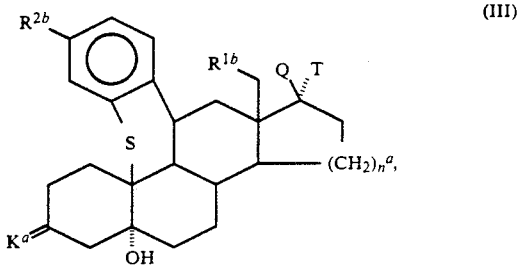

(III)

Thus, a further aspect of this invention is to provide intermediate components of Formula III, wherein $R^{1b}$, $R^{2b}$, $K^a$, and $n^a$ have the same meanings as $R^1$, $R^2$, K and n of Formula I, respectively, but wherein optionally a hydroxy, mercapto, amino, oxo, and/or terminal acetylene group present in $R^{2b}$ is blocked, and Q is $R^5$ and T is $R^6$ and have the same meanings as $R^5$ and $R^6$ of Formula I, or Q and T jointly are a keto oxygen atom.

On the other hand, another embodiment of the process of this invention makes it possible to vary the substituent in the o-phenylene ring over a wide range by introducing the substituent only after cyclization, namely before or after completion of the structure of the A and D rings. For this purpose, the hydroxy group present and blocked in the o-phenylene ring is freed of its blocking group, and the corresponding perfluoroalkyl sulfonate compound is produced from the free OH compound by reaction with perfluoroalkyl sulfonic acid anhydride (alkyl=$C_1$-$C_4$) by using conventional methods [P. J. Stang, M. Hanack and L. R. Subramanian, Synthesis 85 (1982)].

This perfluoroalkyl sulfonate compound is then converted, by reaction with a correspondingly substituted trialkyltin compound, into a compound which, in this case, either a ready exhibits the desired substitution pattern on the phenylene ring or has this pattern imparted to it by additional reaction(s) performed on the substituent introduced via the trialkyltin compounds. The thus-occurring displacement of the perfluoroalkyl sulfonate residue and the introduction of the new substituent from the substituted trialkyltin compound is preferably conducted with catalysis by a transition metal. In this connection, palladium (0) compounds have proven to be especially effective, e.g. tetrakis(triphenylphosphine) palladium (0) (J. E. McMurry and S. Mohanraj, Tetrahedron Letters, 24:2723-2726, No. 27, 1983; X. Lu and J. Zhu, Communications, pp. 726-727, 1987; Q. -Y. Chen and Z. -Y. Yang, Tetrahedron Letters 27:1171-1174, No. 10, 1986; S. Cacchi, P. G. Ciattini, E. Morera and G. Ortar, Tetrahedron Letters 27:3931-3934, No. 33, 1986; A. M. Echavarren and J. K. Stille, J. Am. Chem. Soc. 109:5478-5486, 1987).

Example 4 represents a reaction sequence wherein first of all the corresponding (1-ethoxyvinyl) compound is prepared from the trifluoromethanesulfonate compound by reaction with (1-ethoxyvinyl)tributyltin with the addition of tetrakis(triphenylphosphine) palladium (0), and this product is subsequently converted into the corresponding acetyl compound by acidic cleavage and rearrangement. After renewed blockage of the thus-liberated 3-keto function and of the newly formed keto function in the acetyl substituent in the 5-position of the o-phenylenethio residue, the 17β-OH group can be oxidized and added to the thus-formed keto group in nucleophilic fashion.

However, the process of this invention also makes it possible to introduce the substituent desired at the phenylene ring directly, for example the vinyl substituent by reacting the trifluoromethanesulfonate compound with (vinyl)tributyltin.

Additional examples for reactions possible at the trifluoromethanesulfonate group can be found in the European Patent Application EP-A Publication Number 0283428 (corresponding to PCT/DE 88/00150) and, above all, in the aforementioned publications.

Educts having a D-homo steroid skeleton can be obtained, for example, by Tiffeneau rearrangement analogously to the directions published in Australian J. Chem. 8:519 (1955) and in "Organic Reactions in Steroid Chemistry" vol. 2:388 (1972). The required 17α-amino-methyl-17β-hydroxy compounds are produced, for example, via opening of the 17,20-spiroepoxides with ammonia or also by lithium aluminum reduction of the acetylated 17β-hydroxy-17α-cyano compounds. The spiroepoxides are obtainable by reacting the corresponding 17-ketones with dimethylsulfonium methylide in dimethylformamide [Journal f. prakt. Chemie 314:667-668 (1972)]. The acetylated cyanohydrins can be produced by chemical addition of hydrogen cyanide to the corresponding 17-ketones and subsequent acetylation according to known protocols [e.g. Australian J. Chem. 8:519 (1955)].

Educts having an unsaturated D ring can be obtained, for example, by modified Saegusa oxidation [Tetrahedron 42:2971 (1986)] of the corresponding enol compounds of the 17-ketone. For example, the trimethylsilyl enol ether can be prepared by converting the 17-ketone with lithium diisopropylamide in tetrahydrofuran into the corresponding enolate and scavenging by trimethylchlorosilane (Synthesis 1983:1).

Introduction of the substituents $R^5$ and $R^6$ takes place according to the customary methods of C-17 side chain construction by nucleophilic addition to the 17-ketone obtained, for example, by Oppenauer oxidation of the C-17 hydroxy group and secondary reactions ("Terpenoids and Steroids", Specialist Periodical Report, The Chemical Society, London, vol. 1-12.

Introduction of the substituent —C≡C—U as $R^6$ wherein U has the above-indicated meanings takes place with the aid of a compound of the general formula MC≡C—U' wherein U' is the residue U blocked with a blocking group, e.g. trimethylsilyl or tert-butyldimethylsilyl or wherein, if U is an alkyl group of 1-4 carbon atoms, U' proper represents the residue U.

The organometallic compound can also be formed in situ and made to react with the 17-ketone. Thus, it is possible, for example, to treat the 17-ketone in a suitable solvent with acetylene and an alkali metal, especially potassium, sodium or lithium, in the presence of an alcohol or in the presence of ammonia. The alkali metal can also be used in the treatment in the form of, for example, methyllithium or butyllithium. Especially suitable solvents are dialkyl ethers, tetrahydrofuran, dioxane, benzene and toluene.

The introduction of 3-hydroxypropyne, -propene and, respectively, -propane in the 17-position takes place by reacting the 17-ketone with the dianion of the propargyl alcohol (3-hydroxypropyne), for example with the dipotassium salt of propargyl alcohol formed in situ, to the 17α-(3-hydroxyprop-1-ynyl)-17β-hydroxy derivative or with metalated derivatives of 3-hydroxypropyne, e.g. with 1-lithium-3-(tetrahydropyran--2'-yloxy)prop-1-yn-1-ide, to the 17α-[3-(tetrahydropyran-2'-yloxy)prop-1-ynyl -17β-hydroxy derivative which can then be hydrogenated to the 17-(3-hydroxypropyl- or -hydroxypropenyl)-17β-hydroxy compounds. This is accomplished, for example, by hydrogenation at room temperature and under normal pressure in solvents such as methanol, ethanol, propanol, tetrahydrofuran (THF) or ethyl acetate with the addition of noble metal catalysts such as platinum or palladium.

The introduction of homologous hydroxyalkyne, hydroxyalkene and hydroxyalkane groups takes place correspondingly with homologs of propargyl alcohol.

The compound with the Z-configured double bond in the hydroxypropenyl group is formed by hydrogenation of the acetylenic triple bond with a deactivated noble metal catalyst (J. Fried, J. A. Edwards: Organic Reactions in Steroid Chemistry, Van Nostrand Reinhold Company 1972, p. 134; and H. O. House: Modern Synthetic Reactions 1972, p. 19). Examples of suitable deactivated noble metal catalysts are 10% palladium on barium sulfate in the presence of an amine or 5% palladium on calcium carbonate with the addition of lead(II) acetate. The hydrogenation is interrupted after absorption of one equivalent of hydrogen.

The compound having the E-configured double bond in the hydroxypropenyl group is produced by reduction of the acetylenic triple bond in a manner known per se. Quite a number of methods for converting alkynes into trans-olefins have been described in the literature, for example the reduction with sodium in liquid ammonia [J. Am. Chem. Soc. 63:216 (1941)], with sodium amide in liquid ammonia [J. Chem. Soc. (1955), 3558], with lithium in low-molecular amines [J. A. Chem. Soc. 77:3378 (1955)], with boranes [J. Am. Chem. Soc. 93:3395 (1971) and 94:6560 (1972)], with diisobutyl aluminum hydride and methyllithium [J. Am. Chem. Soc. 89:4245 (1967)}. Another possibility resides in reducing the triple bond with chromium(II) sulfate in the presence of water or dimethylformamide in a weakly acidic medium J. Am. Chem. Soc. 86:4358 (1964)] as well as, in general, reduction under the effect of transition metal compounds with a change in the oxidation stage.

Introduction of the hydroxyalkenes can also be brought about directly by addition of a corresponding metalated hydroxyalkenyl compound, such as, for example, 1-lithium-3-(tetrahydropyran-2'-yloxy)prop-1(E)-ene (J. Org. Chem. 40:2265, (1975)) or 1-lithium-3-(tetrahydropyran-2'-yloxy)prop-1(Z)-ene (Synthesis 1981:999). Homologs can likewise be introduced in this way.

The introduction of 3-hydroxypropane in the 17-position can also take place directly by reacting the 17-ketone with metalated derivatives of 3-halopropanols —wherein the hydroxy group is present in the metalating step as an alcoholate (Tetrahedron Letters 1978:3013) or as a blocked function (J. Org. Chem. 37:1947,(1972))—to obtain the 17-(3-hydroxypropyl)-17β-hydroxy compound or, respectively, the compound blocked at the terminal hydroxy group. Examples of suitable blocking groups are the ethoxyethyl, tetrahydropyranyl and methoxymethyl groups.

If final products of Formula I are desired wherein $R^5/R^6$ mean

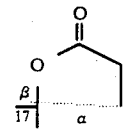

then the 17-(3-hydroxypropyl) compound is oxidized in a manner known per se, for example with Jones reagent, pyrolusite, pyridinium dichromate, pyridinium chlorochromate, chromic acid—pyridine or the Fetizon reagent silver carbonate/"Celite" [Compt. rend. 267:900 (1968)].

Final products of Formula I wherein $R^5/R^6$ mean

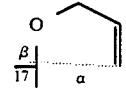

are produced by ring closure reaction of the corresponding 17-(3-hydroxyprop-1 Z)-enyl)-17β-hydroxy educt.

The 17-cyanomethyl side chain is built up conventionally from the 17-ketone, for example via the 17-spiroepoxide and cleavage of the spiroepoxide with HCN according to Z. Chem. 18:259-260 (1978).

Also the introduction of the 17-hydroxyacetyl side chain takes place according to known methods, for example according to the methods disclosed in J. Org. Chem. 47:2993-2995 (1982), Chem. Ber. 113:1184 (1984), and, respectively, U.S. Pat. No. 4,600,538.

In order to introduce the groupings

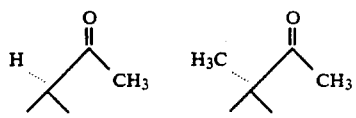

the 17-ketone is converted, with tosylmethylisocyanide (Chem. Ind. 1972:213), into the 17-nitrile compound Tetrahedron 31:2151 (1975)] which latter can be converted directly into the 17-acetyl compound with methyllithium or methylmagnesium bromide; the 17-acetyl compound yields, after enolizing with potassium tert-butylate in tetrahydrofuran and reaction with methyl iodide, the desired 17α-methyl-17β-acyl grouping. This sequence of methyl addition to the nitrile and subsequent alkylation can also be executed in reverse order.

Free hydroxy or mercapto and/or amino groups present in Z and, respectively, on the phenylene ring can be conventionally alkylated or acylated.

Besides the already described method, it is possible to convert compounds having a dialkylamine substituent on the phenylene ring in good yields into the corresponding (N-cyano-N-alkylaminoaryl) derivatives by reaction with cyanogen bromide in aprotic solvents, such as, for example, dioxane, benzene or toluene at an elevated temperature (amine degradation according to Braun) in analogy to the directions set forth, for example, in Org. Reactions 7:198 (1953), K. W. Bentley, Techniques of Organic Chemistry 11:773 (1963), and Houben-Weyl, 5/4:151 (1960).

The resultant compounds of Formula I wherein X means an oxygen atom can be converted, if desired, into the oximes (Formula I where X means the hydroxyimino grouping N O wherein the hydroxy group can be syn- or anti-positioned) by reaction with hydroxylamine hydrochloride in the presence of tertiary amines at temperatures of between −20° and +40° C. Suitable tertiary bases are, for example, trimethylamine, triethylamine, pyridine, N,N-dimethylaminopyridine, 1,5-diazabicyclo[4.3.0]nonene-5 (DBN) and 1,5-diazabicyclo[5.4.0]undecene-5 (DBU), pyridine being preferred.

Various methods for introducing and removing a variety of blocking groups where required can be found in *Protective Groups in Organic Synthesis*, Theodore W. Green, ed., John Wiley, N.Y. (1981), as well as methods which can be found in "Terpenoids and Steroids," supra.

The novel compounds of Formula I, as well as their pharmaceutically compatible addition salts with acids, have valuable pharmaceutical properties. Thus, they exhibit strong affinity to the gestagen receptor and display a surprisingly large range of antigestagen and antiglucocorticoid properties. These important bioactivities can be exploited, e.g., in the field of human and veterinary medicine.

In view of the antigestagenic activity of the active agents, they are suitable for inducing abortion, since they displace progesterone required to sustain pregnancy, from the receptor. For this reason, they are valuable and of interest with a view toward their use for postcoital fertility control. Antigestagenic activity can be routinely determined in each case by use of a conventional pharmacological protocol which measures the ability of a compound to interact with gestagen receptors. Such protocols are described in Fertility and Sterility 40, 253 (1982), Steroids 37, 361 (1981), and U.S. Pat. No. 4,519,946.

They can also be used to treat hormonal irregularities, for inducing menstruation, and for inducing labor.

Furthermore, they can be utilized for the treatment of hormone-dependent carcinomas.

The compounds of Formula I according to this invention, as well as their pharmaceutically compatible acid addition salts, also show antiglucocorticoid activity and, thus, can likewise be used as medicinal agents for the therapy of corticoid-induced disturbances (e.g., glaucoma), as well as for combatting side effects occurring upon long-term treatment with glucocorticoids (e.g., Cushing's syndrome). Therefore, they also are useful in the treatment of disorders which are due to supersecretion of the glucocorticoids; for example, adipositas, arteriosclerosis, hypertension, osteoporosis, and diabetes, as well as insomnia. Antiglucocorticoid activity can be routinely determined in each case by use of a conventional pharmacological protocol. Such protocols are described in U.S. Pat. No. 4,519,946 and G.B. 2,118,186.

Consequently, the invention also concerns medicinal agents based on the pharmaceutically acceptable compounds of Formula I, i.e., compounds that are not toxic in the dosages utilized, as well as the pharmaceutically compatible acid addition salts thereof, optionally together with the usual auxiliary agents and excipients, for administration to patients, e.g., mammals, including humans.

The compounds of this invention and their salts can be processed according to conventional methods of galenic pharmacy into pharmaceutical preparations for enteral, percutaneous, parenteral, or local administration. They can be administered in the form of tablets, dragees, gelcaps, granules, suppositories, implants, syrups, injectable sterile aqueous or oily solutions, suspensions or emulsions, ointments, creams, and gels. Ampoules are convenient unit dosages.

The active ingredient or ingredients can be mixed with the auxiliary compounds customary in galenic pharmacy, e.g., gum arabic, talc, amylose, mannitol, methylcellulose, lactose, tensides such as "Tweens" or "Myrj", magnesium stearate, aqueous or nonaqueous vehicles, paraffin derivatives, and aromatous compounds for flavor amelioration (for example, ethereal oils).

Sustained or directed release compositions can be formulated, e.g., liposomes or those wherein the active compound is protected with differentially degradable coatings. e.g., by microencapsulation, multiple coatings, etc. It is also possible to freeze-dry the new compounds and use the lyophilizates obtained, for example, for the preparation of products for injection.

For topical application, they are employed as nonsprayable forms, viscous to semi-solid, or solid forms comprising a carrier compatible with topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g., preservatives, stabilizers, wetting agents, buffers, or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon.

Therefore, the invention also relates to pharmaceutical compositions containing as the active ingredient at least one compound of this invention or one of its pharmaceutically compatible acid addition salts.

The hydrochlorides and the methanesulfonates can be cited, in particular, as additional salts of the products of this invention with acids.

Generally, the compounds of this invention are dispensed in unit dosage form comprising 1 to 100 mg in a pharmaceutically acceptable carrier per unit dosage. They are incorporated in topical formulations in concentrations of about 2 to 40 weight percent; for example, from 1 μg of active ingredient in a 50 μg formulation to up to 100 μg of active ingredient in a total of 250 μg.

The preferred dosage ranges for the compounds of this invention when used for the above-described activities are as follows:

a) Antigestagenic activity: 1–1000 mg/day, preferably 20–200, analogously to the known agent RU 38,486 b) Antiglucocorticoid activity: 10–1000 mg/day, preferably 50–1000, analogously to the known agent RU 38,486.

It will be appreciated that the actual preferred amounts of active compound in a specific case will vary according to the specific compound being utilized, the particular compositions formulated, the mode of application, and the particular situs and organism being treated. Dosages for a given host can be determined using conventional considerations, e.g., by customary comparison of the differential activities of the subject compounds and of a known agent, e.g., by means of an appropriate, conventional pharmacological protocol.

As a representative for all compounds of this invention, the abortive effect of the compound of Example 6C was determined for characterizing the antigestagen activity:

The experiments were conducted on female rats weighing about 200 g. After mating had taken place, the beginning of pregnancy was confirmed by detecting sperm in vaginal smears. The day of sperm detection is considered day 1 of gravidity (=d1 p.c.; p.c.=postcoitus).

The animals were treated with the compound to be tested or, respectively, the solvent, after nidation of the blastocysts, from d5 p.c. to d7 p.c. On d9 p.c., the animals were sacrificed and the uteri examined for implants and absorption sites. Photos were made of all uteri. The lack of implants, pathological, hemorrhagic, or otherwise abnormal nidation sites was evaluated as abortion.

The test compound was dissolved in a benzyl benzoate-castor oil mixture (proportion 1+4). The vehicle volume per single dose was 0.2 ml. Treatment was effected subcutaneously.

With a dosage of 3.0 mg/animal/day, this compound was fully effective abortively (n abortion/n test animals treated 4/4; solvent control 0/4).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, and of corresponding West German Application No. P 38 20 948.9, filed June 16, 1988, are hereby incorporated by reference.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

EXAMPLES

Unless indicated otherwise, the purification steps in the subsequent examples involving column chromatography are performed on aluminum oxide of activity stage III with hexane/ethyl acetate, optionally with a gradient mixture of increasing polarity.

EXAMPLE 1

Production of 17β-Hydroxy-10β,11β-(5-methoxy-o-phenylenethio)-estr-4-en-3-one (1C)

A.

10β-(2-Bromo-5-methoxyphenylthio)-3,3-(2,2-dimethyltrimethylenedioxy)estr-9(11)-ene-5α,17β-diol (1A)

22.3 g of 2-bromo-5-methoxythiophenol is dissolved in 182 ml of absolute THF and combined at −40° C. with 40 ml of a 2.5-molar n-butyllithium solution in hexane. Cooling is discontinued and the mixture is stirred for 30 minutes. At this point in time, 12.73 g of 3,3-(2,2-dimethyltrimethylenedioxy)-5α,10α-epoxyestr-9(11)-en-17β-ol, dissolved in 100 ml of absolute THF, is added dropwise, the temperature being maintained at 0° C. Subsequently, the mixture is further stirred for 2 hours at room temperature.

The reaction mixture is combined with 300 ml of saturated NH₄Cl solution and extracted with ethyl acetate, the organic phase is washed with water and dried over Na₂SO₄, and the solvent is removed under vacuum.

Column chromatography yields 17.99 g of 1A; mp 117°–119° C.

B.

3,3-(2,2-Dimethyltrimethylenedioxy)-10β,11β-(5-methoxy-o-phenylenethio)estrane-5α,17β-diol (1B)

2.3 g of 1A, 1.25 g of tributyltin hydride and 25 mg of azobisisobutyronitrile are stirred in 50 ml of toluene p.a. under argon and refluxed for one hour under the light of a 300 watt incandescent bulb.

Column chromatography yields 1.09 g of 1B; mp 95°–97° C.

C.

17β-Hydroxy-10β,11β-(5-methoxy-o-phenylenethio)-estr-4-en-3-one (1C)

600 mg (1.2 millimoles) of 1B and 1.1 ml of 4N HCl are stirred in 22 ml of acetone p.a. (p.a.=analytically pure) for 1.5 hours under reflux.

The reaction solution is combined with NaHCO₃ solution and ethyl acetate, the organic phase is separated, the aqueous phase is washed with ethyl acetate, the combined organic phases are washed with water and dried over sodium sulfate, and the solvent is removed under vacuum.

Column chromatography yields 364 mg of 1C; mp 85°–88° C.

EXAMPLE 2

Production of
17β-Hydroxy-10β,11β-(5-methoxy-o-phenylenethio)-
17β-(1-propynyl)estr-4-en-3-one (2C)

A.

3.3-(2,2-Dimethyltrimethylenedioxy)-5α-hydroxy-
10β,11β-(5-methoxy-o-phenylenethio)estran-17-one
(2A)

1.24 g of 1B is dissolved in 52 ml of toluene p.a., combined with 174 mg of aluminum triisopropylate and 1.1 ml of cyclohexanone and heated for 4.5 hours with reflux on a water trap. If necessary, another equivalent of aluminum triisopropylate is added and the mixture stirred for several hours more.

The reaction solution is diluted with water, extracted with ethyl acetate, the organic phase is washed with water, dried over sodium sulfate and concentrated under vacuum.

Column chromatography yields 0.82 g of 2A; mp 249°-250° C.

B.

3,3-(2,2-Dimethyltrimethylenedioxy)-10β,11β-(5-methoxy-o-phenylenethio)-17α-(1-propynyl)-estrane-5α,17β-diol (2B)

A stream of propyne is passed through 11 ml of absolute THF at 0° C. for a period of 1.5 hours; 3 ml of n-butyllithium (2.5-molar in hexane) is added dropwise to this solution, the latter is stirred for 90 minutes at 0° C., 640 mg (1.25 mmol) of 2A in 30 ml of absolute THF is added, and the mixture is stirred for another hour at room temperature.

The reaction solution is combined with 25 ml of water, extracted with ethyl acetate, the organic phase is washed with water, dried over sodium sulfate and concentrated under vacuum.

Yield after column chromatography: 690 mg of 2B as a foam.

C.

17β-Hydroxy-10β,11β-(5-methoxy-o-phenylenethio)-
17α-(1-propynyl)estr-4-en-3-one (2C)

690 mg of 2B is dissolved in 25 ml of acetone p.a. and stirred with 1.27 ml of 4N HCl for 4.5 hours at 60° C.

The reaction solution is combined with saturated NaHCO₃ solution, extracted with ethyl acetate, the organic phase is washed with water, dried over sodium sulfate, the solvent is removed under vacuum.

Column chromatography yields 330 mg of 2C; mp 254°-257° C.

EXAMPLE 3

Production of
10β,11β-(5-Diethylamino-o-phenylenethio)-17β-
hydroxy-17α-(1-propynyl)estr-4-en-3-one (3K)

A.

10β-(3-Aminophenylthio)-3,3-(2,2-dimethyltrimethylenedioxy)estr-9(11)-ene-5α,17β-diol (3A)

The process and working up steps are performed as described in Example 1A.

Amounts utilized: 500 mg of 3,3-(2,2-dimethyltrimethylenedioxy)-5α,10α-epoxyestr-9(11)-en-17β-ol (in 4 ml of absolute THF), 750 mg of 3-mercaptoaniline (in 5 ml of absolute THF), 3.73 ml of 1.6-molar n-butyllithium in hexane.

Yield after column chromatography: 484 mg of 3A as a foam.

B.

17β-Acetoxy-10β-(3-acetylaminophenylthio)-3,3-(2,2-dimethyltrimethylenedioxy)estr-9(11)-en-5α-ol (3B)

7.3 g of 3A and 44 ml of acetic anhydride are agitated in 73 ml of pyridine p.a. at room temperature for 4 hours under argon.

The reaction solution is diluted with methylene chloride and combined with NaHCO₃ solution; the organic phase is separated, washed with water, and dried over sodium sulfate; and the solvent is withdrawn under vacuum. Yield after column chromatography: 7.65 g of 3B as a foam.

C.

3,3-(2,2-Dimethyltrimethylenedioxy)-10β-(3-ethylaminophenylthio)estr-9(11)-ene-5α,17β-diol (3C)

7 g of 3B and 2.9 g of lithium aluminum hydride are stirred under reflux in 250 ml of absolute ether for hours at 50° C. under argon.

The excess lithium aluminum hydride is hydrolyzed under ice cooling with water, the organic phase is separated, the aqueous phase is washed with ethyl acetate, the combined organic phases are washed with water and dried over sodium sulfate, and the solvent is evaporated.

Yield after column chromatography: 5.37 g of 3C; mp 100° C.

D.

17β-Acetoxy-10β-(3-N-acetyl-N-ethylaminophenylthio)-3,3-(2,2-dimethyltrimethylenedioxy)estr-9(11)-en-5α-ol (3D)

The process and working up steps are performed as described in Example 3B.

Amounts utilized: 5.3 g of 3C, 38 ml of acetic anhydride, 53 ml of pyridine p.a.

Yield after column chromatography: 4.76 g of 3D; mp 188° C.

E.

10β-(3-Diethylaminophenylthio)-3,3-(2,2-dimethyltrimethylenedioxy)estr-9(11)-ene-5α,17β-diol (3E)

The process and working up steps are carried out as in Example 3C.

Amounts used: 3.2 g of 3D, 1.4 g of lithium aluminum hydride, 100 ml of THF, 20 ml of ether.

Yield after column chromatography: 2.72 g of 3E; mp 104° C.

F.

10β-(2-Bromo-5-diethylaminophenylthio)-3,3-(2,2-dimethyltrimethylenedioxy)estr-9(11)-ene-5α,17β-diol (3F)

556 mg of 3E and 175 mg of N-bromosuccinimide are stirred in 6 ml of CCl₄ for 2 hours at 0° C. under argon.

Then the mixture is combined with NaHCO₃ solution and taken up in methylene chloride; the organic phase is separated; the aqueous phase is washed with methylene chloride; the combined organic phases are washed with water and dried over sodium sulfate; and the solvent is evaporated.

Yield after column chromatography: 510 mg of 3F; mp 115° C.

G.

10β,11β-(5Diethylamino-o-phenylenethio)-3,3-(2,2-dimethyltrimethylenedioxy)estrane-5α,17β-diol (3G)

The process and working up steps are conducted as in Example 1B.

Amounts utilized: 250 mg of 3F, 126 mg of tributyltin hydride and 2 mg of azobisisobutyronitrile in 16 ml of toluene p.a.

Yield after column chromatography: 102 mg of 3G as a white foam.

H.

10β,11β-(5-Diethylamino-o-phenylenethio)-3,3-(2,2-dimethyltrimethylenedioxy)-5α-hydroxyestran-17-one (3H)

The process and working up steps are performed as in Example 2A.

Amounts utilized: 555 mg of 3G in 25 ml of toluene p.a., 100 mg of aluminum triisopropylate, 0.46 ml of cyclohexanone.

Yield after column chromatography: 430 mg of 3H; mp 271° C.

I.

10β,11β-(5-Diethylamino-o-phenylenethio)-3,3-(2,2-dimethyltrimethylenedioxy)-17α-(1-propynyl)estrane-5α,17β-diol (3I)

The process and working up steps are carried out as in Example 2B.

Amounts used: 860 mg of 3H in 20 ml of absolute THF, 50 ml of absolute THF, 2 hour long propyne stream, 3.7 ml of n-butyllithium (2.5-molar in hexane).

Yield after column chromatography: 880 mg of 3I as a foam.

K.

10β,11β-(5-Diethylamino-o-phenylenethio)-17β-hydroxy-17α-(1-propynyl)estr-4-en-3-one (3K)

The process and working up steps are performed as in Example 2C.

Amounts used: 880 mg of 3I, 28 ml of acetone p.a., 1.4 ml of 4N HCl.

Yield after column chromatography: 548 mg of 3K as a foam.

$^1$H NMR Spectrum (CD$_2$Cl$_2$, 300 MHz):δ(in ppm) 0.45 (s, H-18),
1.90 (s, H-22), 3.30 (q, N—CH$_2$—CH$_3$), 1.15 (t, N—CH$_2$—CH$_3$),
3.40 (ddbr, H-11), 5.90 (sbr, H-4), 7.25 (d, H-3'), 6.45 (dd, H-4'), 6.3 (d, H-6').

EXAMPLE 4

Production of 10β,11β-(5-Acetyl-o-phenylenethio)-17β-hydroxy-17α-(1-propynyl)estr-4-en-3-one (4H)

A.

3,3-(2,2-Dimethyltrimethylenedioxy)-10β,11β-(5-hydroxy-o-phenylenethio)estrane-5α,17β-diol (4A)

500 mg of 1B is dissolved in 5 ml of distilled dimethylformamide and stirred under reflux with 293 mg of sodium methanethiolate for 4 hours at 160° C. The reaction solution is combined with saturated NaHCO$_3$ solution and extracted with methylene chloride, the organic phase is washed with water and dried over sodium sulfate, and the solvent is removed under vacuum.

Yield after column chromatography on SiO$_2$ with hexane/ethyl acetate: 330 mg of 4A; mp 271° C.

B.

3,3-(2,2-Dimethyltrimethylenedioxy)-10β,11β-(5-trifluoromethylsulfonyloxy-o-phenylenethio)estrane-5α,17β-diol (4B)

2.53 g of 4A and 3.43 g of dimethylaminopyridine are dissolved in 75 ml of methylene chloride and combined at −30° C. under argon with 0.12 ml of trifluoromethanesulfonic anhydride. The mixture is further stirred for 10 minutes. The reaction solution is poured into water and extracted with methylene chloride, the organic phase is washed with water and dried over sodium sulfate, and the solvent is withdrawn under vacuum.

Yield after column chromatography on SiO$_2$ with hexane/ethyl acetate: 2.56 g of 4B, mp 189° C.

C.

3,3-(2,2-Dimethyltrimethylenedioxy)-10β,11β-[5-(1-ethoxyethenyl)-o-phenylenethio]estrane-5α,17β-diol (4C1) and 10β,11β-(5-Acetyl-o-phenylenethio)-3,3-(2,2-dimethyltrimethylenedioxy)estrane-5α,17β-diol (4C2)

2.55 g of 4B is dissolved in 60 ml of dimethylformamide, combined with 338 mg of LiCl, 1.51 ml of (1-ethoxyvinyl)tributyltin and 95 mg of tetrakis(triphenylphospine) palladium (O) and stirred at 110° C. for 2 hours under argon.

After cooling, the reaction solution is poured on saturated NaHCO$_3$ solution, extracted with ethyl acetate, washed with saturated NaCl solution, and dried over Na$_2$SO$_4$.

Yield: 2.5 g of a mixture of 4C1 and 4C2 in a proportion of about 1:2 as a foam.

4C2 is formed in this process from 4C1 during the working up step and during the step of purification by column chromatography.

D.

10β,11β-(5-Acetyl-o-phenylenethio)-17β-hydroxy-estr-4-en-3-one (4D)

2.24 g of the mixture of 4C1 and 4C2 (proportion about 1:2) is dissolved in 92 ml of acetone p.a., combined with 1.6 ml of concentrated HCl, and stirred at 60° C. for 30 minutes. The reaction solution is then combined with saturated NaHCO$_3$ solution, taken up in ethyl acetate, dried over Na$_2$SO$_4$, and concentrated on a rotary evaporator.

Yield after column chromatography on SiO$_2$ with hexane/ethyl acetate: 1.02 g of 4D (foam).

E.

3,3-(2,2-Dimethyltrimethylenedioxy)-10β,11β-[5-[1,1-(2,2-dimethyltrimethylenedioxy)ethyl]-o-phenylenethio]estr-5-en-17β-ol (4E)

1.15 g of 4D is dissolved in 30 ml of toluene p.a., combined with 2.82 g of 1,3-dimethylpropanediol and 206 mg of p-toluenesulfonic acid and heated under reflux on a water trap for 2 hours under argon.

After cooling, the reaction solution is combined with 1N NaOH, taken up in ethyl acetate, washed with saturated NaHCO$_3$, dried over Na$_2$SO$_4$, and concentrated on a rotary evaporator.

Yield after column chromatography: 1.5 g, mp 177° C.

F. 3,3-(2,2 Dimethyltrimethylenedioxy)-10β,11β-[5-[1,1-(2,2-dimethyltrimethylenedioxy)ethyl]-o-phenylenethio]estr-5-en-17-one (4F)

The process and working up steps are conducted as in case of Example 2A.

Amounts used: 1.5 g of 4E, 70 ml of toluene p.a., 1.95 ml of cyclohexanone, 300 mg of aluminum triisopropylate.

Yield after column chromatography: 1.2 g of 4F; mp 169° C.

G. 3,3-(2,2-Dimethyltrimethylenedioxy)-10β,11β-[5-[1,1-(2,2-dimethyltrimethylenedioxy)ethyl]-o-phenylenethio]-17α-(1-propynyl)estr-5-en-17β-ol (4G)

The process and working up step are performed as in Example 2B.

Amounts utilized: 17 ml of THF absolute, 2 hour propyne stream, 3.8 ml of n-butyllithium (1.6-molar in hexane), 600 mg of 4F in 17 ml of THF absolute.

Yield after column chromatography: 620 mg of 4G, mp 186° C.

H. 10β,11β-(5-Acetyl-o-phenylenethio)-17β-hydroxy-17α-(1-propynyl)estr-4-en-3-one (∝ H)

The process and working up steps are conducted as in Example 2C.

Amounts used: 620 mg of 4G, 23 ml of acetone p.a., 1.55 ml of 4N HCl.

Yield: 347 mg of 4H (after column chromatography), mp 174° C.

EXAMPLE 5

Production of 10β,11β-(5-Dimethylamino-o-phenylenethio)-17β-hydroxy-17α-(1-propynyl)estr-4-en-3-one (5I)

A. 3,3-(2,2-Dimethyltrimethylenedioxy)-10β-(3-formylaminophenylthio)estr-9(11)-ene-5α,17β-diol (5A)

0.4 ml of acetic anhydride and 0.17 ml of HCOOH are combined and stirred at room temperature under argon for 15 minutes. This solution is combined with 1.0 g of 3A, dissolved in 5 ml of pyridine p.a., and agitated at room temperature under argon for another 2 hours.

Then the reaction mixture is taken up in ethyl acetate, shaken with saturated NaHCO₃ solution until a pH of about 8 has been attained, washed with water, dried over Na₂SO₄, and concentrated by means of a rotary evaporator.

Yield after column chromatography: 935 mg of 5A, foam.

B. 3,3-(2,2-Dimethyltrimethylenedioxy)-10β-(3-methylaminophenylthio)estr-9(11)-ene-5α,17β-diol (5B)

9.4 g of 5A and 2.5 g of lithium aluminum hydride are heated under reflux in 400 ml of THF absolute at 80° C. under argon for one hour.

Subsequently excess lithium aluminum hydride is hydrolyzed with water, diluted with ethyl acetate, the organic phase is separated and washed with water, dried over Na₂SO₄, and the solvent evaporated by means of a rotary-evaporator.

Yield after column chromatography: 8.4 g of 5B, foam.

C. 3,3-(2,2-Dimethyltrimethylenedioxy)-10β-(3-N-formyl-N-methylaminophenylthio)estr-9(11)-ene-5α,17β-diol (5C)

The process and working up step are conducted as in Example 5A.

Amounts used: 8.6 g of 5B, 3.39 ml of acetic anhydride, 1.4 ml of HCOOH, 45 ml of pyridine p.a.

Yield after column chromatography: 6.0 g of 5C, foam.

D. 10β-(3-Dimethylaminophenylthio)-3,3-(2,2-dimethyltrimethylenedioxy)estr-9(11)-ene-5α,17β-diol (5D)

3.95 g of 5C is dissolved in 150 ml of absolute THF and combined at 0° C. under argon with 1.46 ml of a 10-molar borane dimethyl sulfide complex solution in THF. The mixture is stirred for 2.5 hours at room temperature. The reaction mixture is combined at 0° C. gradually with 4 ml of methanol and allowed to stand overnight in the open air. Then the mixture is diluted with H₂O and ethyl acetate. The organic phase is separated, washed with H₂O, dried over Na₂SO₄, and concentrated under vacuum.

Yield after column chromatography: 3.6 g of 5D, foam.

E. 10β-(2-Bromo-5-dimethylaminophenylthio)-3,3-(2,2-dimethyltrimethylenedioxy)estr-9(11)-ene-5α,17β-diol (5E)

5 g of 5D is dissolved in 200 ml of CCl₄, combined at 0° C. with 1.65 g of N-bromosuccinimide, and stirred under argon at 0° C. for 2 hours. The reaction mixture is diluted with CH₂Cl₂ and combined with saturated NaHCO₃ solution, the organic phase is washed with water and dried over Na₂SO₄, and the solvent is removed by way of a rotary evaporator.

Yield after column chromatography: 2.7 g of 5E, foam.

F. 10β,11β-(5-Dimethylamino-o-phenylenethio)-3,3-(2,2-dimethyltrimethylenedioxy)estrane-5α,17β-diol (5F)

The process and working up steps are performed as in Example 1B.

Amounts used: 1.7 g of 5E, 1.15 ml of tri-n-butyltin hydride, 30 mg of azobisisobutyronitrile, 113 ml of toluene p.a.

Yield after column chromatography: 675 mg of 5F, foam.

G. 10β,11β-(5-Dimethylamino-o-phenylenethio)-3,3-(2,2-dimethyltrimethylenedioxy)-5α-hydroxyestran-17-one (5G)

The process and working up steps are conducted as in Example 2A.

Amounts utilized: 663 mg of 5F, 150 mg of aluminum triisopropylate, 0.578 ml of cyclohexanone, 31 ml of toluene p.a.

Yield after column chromatography: 392 mg of 5G, foam.

H.

10β,11β-(5-Dimethylamino-o-phenylenethio)-3,3-(2,2-dimethyltrimethylenedioxy)-17α-(1-propynyl)estrane-5α,17β-diol (5H)

The process and working up steps are performed as in Example 2B.

Amounts used: 15 ml of THF absolute, 1 hour long propyne stream, 2.8 ml of n-butyllithium (1.6-molar in hexane), 390 mg of 5G in 10 ml of absolute THF.

Yield after column chromatography: 350 mg of 5H.

I.

10β,11β-(5-Dimethylamino-o-phenylenethio)-17β-hydroxy-17α-(1-propynyl)estr-4-en-3-one (5I)

The process and working up steps are conducted as in Example 2C.

Amounts utilized: 340 mg of 5H, 11 ml of acetone p.a., 0.54 ml of 4N HCl.

Yield after column chromatography: 185 mg of 5I, foam.

$^1$H NMR Spectrum (CD$_2$Cl$_2$, 300 MHz:δ(in ppm) 0.40 (s, H-18), 1.90 (s, H-22), 3.40 (ddbr, H-11), 5.85 (s, H-4), 2.88 (s, N—CH$_3$), 7.31 (d, 10 Hz, H-3'), 6.53 (dd, 10.2 Hz, H-4'), 6.38 (d, 2 Hz, H-6').

EXAMPLE 6

Production of
10β,11β-(5-N,N-Dimethylamino-o-phenylenethio)-17β-hydroxy-17α-(3-hydroxyprop-1(Z)-enyl)estr-4-en-3-one (6C)

A.

10β,11β-(5-N,N-Dimethylamino-o-phenylenethio)-3,3-(2,2-dimethyltrimethylenedioxy)-17β-[3-(tetrahydropyran-2-yloxy)-1-propynyl]estrane-5α,17β-diol (6A)

3.44 ml of propargyl-THP ether is added to 120 ml of absolute tetrahydrofuran and combined at 0° C. under argon with 14.4 ml of n-butyllithium (1.6-molar in hexane). After this adding step, the mixture is stirred for 30 minutes at 0° C., 1.23 g of 5G in 30 ml of absolute tetrahydrofuran is added, and then the mixture is agitated at room temperature for 16 hours. The reaction mixture is combined with saturated NH$_4$Cl solution and diluted with ethyl acetate. The organic phase is separated, washed first with saturated NaCl solution, then with water, dried over sodium sulfate, and concentrated under vacuum.

Yield after column chromatography: 890 mg of 6A as a foam.

B.

10β,11β-(5-N,N-Dimethylamino-o-phenylenethio)-3,3-(2,2-dimethyltrimethylenedioxy)-17α-[3-(tetrahydropyran-2-yloxy)prop-1(Z)-enyl]estrane-5α,17β-diol (6B)

850 mg of 6A is added to 8.5 ml of ethanol p.a. and 8.5 ml of pyridine p.a. and combined, under argon, with 85 mg of palladium on barium sulfate as the catalyst. Then the mixture is hydrogenated for 16 hours at room temperature under mechanical shaking. After hydrogen absorption is completed, the catalyst is suctioned off through "Celite" and the filtrate is concentrated under vacuum.

Yield after column chromatography: 650 mg of 6B as a foam.

C.

10β,11β-(5-N,N-dimethylamino-o-phenylenethio)-17β-hydroxy-17α-(3-hydroxyprop-1(Z)-enyl)estr-4-en-3-one (6C)

600 mg of 6B is dissolved in 25 ml of acetone p.a., combined with 1.4 ml of 4N HCl, and stirred for 15 minutes at 60° C. The reaction solution is combined with saturated NaHCO$_3$ solution and extracted with ethyl acetate. The organic phase is washed with water, dried over Na$_2$SO$_4$, and concentrated under vacuum.

Yield after column chromatography: 255 mg of 6C as a foam.

$^1$H NMR Spectrum (CD$_2$Cl$_2$, 300 MHz:δ(in ppm) 0.49
(s, H-18), 2.9 (s, CH$_3$—N), 3.36 (ddbr, H-11),
4.28 (m, H-22, H-21), 5.68 (m, H-20, H-21),
5.85 (s, H-4), 6.48 (d, 2 Hz, H-6'), 6.52 (dd 10.2Hz, H-4'), 7.3 (d, 10 Hz, H-3').

EXAMPLE 7

Production of
10β,11β-(5-Acetyl-o-phenylenethio)-17β-hydroxy-17α-(3-hydroxyprop-1(Z)-enyl)estr-4-en-3-one (7C)

A.

3,3-(2,2-Dimethyltrimethylenedioxy)-10β,11β-[5-[1,1-(2,2-dimethyltrimethylenedioxy)ethyl]-o-phenylenethio]-17α-[3-(tetrahydropyran-2-yloxy)-1-propynyl]estr-5-en-17β-ol (7A)

The process and working up steps are performed as in Example 6A.

Amounts utilized: 2.5 ml of propargyl-THP ether in 85 ml of absolute tetrahydrofuran, 10.5 ml of n-butyllithium (1.6-molar in hexane), 1.0 g of 4F in 17.5 ml of absolute tetrahydrofuran.

Yield after column chromatography: 1.08 g of 7A, mp 156°–157° C.

B.

10β,11β-(5-Acetyl-o-phenylenethio)-17β-hydroxy-17α-(3-hydroxy-1-propynyl)estr-4-en-3-one (7B)

760 mg of 7A is dissolved in 26 ml of acetone p.a., combined with 1.56 ml of 4N HCl, and stirred for 40 minutes at room temperature as well as another 10 minutes at 60° C. The mixture is worked up as described in Example 6C.

Yield after column chromatography: 341 mg of 7B as a foam.

C.

10β,11β-(5-Acetyl-o-phenylenethio)-17β-hydroxy-17α-(3-hydroxyprop-1(Z)-enyl)estr-4-en-3-one (7C)

The process and working up steps are conducted as in Example 6B.

Quantities employed: 340 mg of 7B, dissolved in 5.3 ml of ethanol p.a., 5.3 ml of pyridine p.a., 53 mg of palladium on barium sulfate.

Yield after column chromatography: 148 mg of 7C as a foam.

$^1$H NMR Spectrum (CD$_2$Cl$_2$, 300 MHz:δ(in ppm)
0.4 (s, H-18), 2.55 (s, H-Ac), 3.47 (ddbr, H-11), 4.3 (m, H-22), 5.7 (m, H-20, H-21), 5.9 (S, H-4),
7.65 (m, H-3', H-4', H-6').

Analogously to the compounds of the above-described examples, the following compounds of this invention can likewise be prepared, inter alia, and comprise the subject of the present invention:

17β-hydroxy-17α-(3-hydroxyprop-1(Z)-enyl)-10β,11β-(5-methoxy-o-phenylenethio)estr-4-en-3-one, 10β,11β-(5-dimethylamino-o-phenylenethio)-17β-hydroxy-17α-methoxymethylestr-4-en-3-one, 17α-cyanomethyl-10β,11β-(5-dimethylamino-o-phenylenethio)-17β-hydroxyestr-4-en-3-one, 10β,11β-(5-dimethylamino-o-phenylenethio)-17β-hydroxy-17α-(3-hydroxyprop-1(Z)-enyl)estr-4-en-3-one, 10β,11β-(5-acetyl-o-phenylenethio)-17β-hydroxyestr-4-en-3-one, 10β,11β-(5-acetyl-o-phenylenethio)-17β-hydroxy-17α-methoxymethylestr-4-en-3-one, 10β,11β-(5-acetyl-o-phenylenethio)-17α-cyanomethyl-17β-hydroxyestr-4-en-3-one, 10β,11β-(5-acetyl-o-phenylenethio)-17β-hydroxy-17α-(3-hydroxyprop-1(Z)-enyl)estr-4-en-3-one, 10β,11β-(5-isopropenyl-o-phenylenethio)-17β-hydroxy-17α-methoxymethylestr-4-en-3-one, 17α-cyanomethyl-10β,11β-(5-isopropenyl-o-phenylenethio)-17β-hydroxyestr-4-en-3-one, 10β,11β-(5-isopropenyl-o-phenylenethio)-17β-hydroxy-17α-(3-hydroxyprop-1(Z)-enyl)estr-4-en-3-one, 10β,11β-(5-ethynyl-o-phenylenethio)-17β-hydroxy-17α-(1-propynyl)estr-4-en-3-one.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A 10β,11β-bridged steroid of the Formula

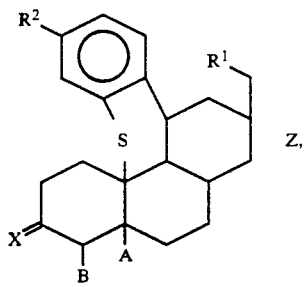

(I)

wherein $R^1$ is H or methyl;

$R^2$ is H; cyano; heteroaryl having 1-2 rings, each ring having 1-3 heteroatoms of O, N or S, and having 3-8 carbon atoms; an aliphatic group of up to 20 carbon atoms; an aliphatic group of up to 20 carbon atoms substituted by oxo; a $C_{4-7}$ cycloalkyl or $C_{4-7}$ cycloalkenyl group; an $OR^3$—, $SR^3$—, —$OSO_2$—$R^{11}$, or $NR^3R^4$-group; or a 4-cyano-, 4-methoxy- or 4-dimethylamino-substituted phenyl group;

$R^3$ is H or a $C_1$-$C_8$-alkyl residue, $R^4$ is an $R^3$ group, cyano or a $C_1$-$C_{10}$-alkanoyl residue, or $R^3$ and $R^4$ jointly with the inclusion of N is a 5- or 6-membered heterocyclic ring wherein the ring can additionally contain a further heteroatom N, O, or S;

$R^{11}$ is a perfluorinated $C_1$-$C_4$-alkyl group;

A and B either jointly are a further bond between C4 and C5, or A is an α-hydroxy group and B is H;

X is keto or oxime group; and

Z is a pentagonal or hexagonal ring residue of the formula

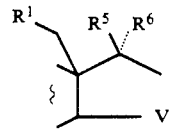

wherein $R^1$ is H or methyl;

—— is a single or double bond;

V is —$CH_2$—, —CH=, —$CH_2CH_2$—, or —$CH_2$—CH=; and $R^5$ and $R^6$ are, respectively, —$OR^7$ and —C≡C—U, —$OR^7$ and

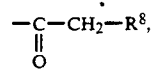

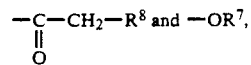

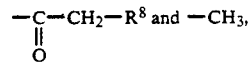

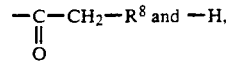

—$OR^7$ and —$(CH_2)_m$—$CH_2$—$R^9$,
—$OR^7$ and —CH=CH$(CH_2)_k$—$CH_2$—$R^9$,
—$OR^{10}$ and —H, or
—$OR^{10}$/ and —$(CH_2)_k$—C≡C—E, wherein E is halogen,

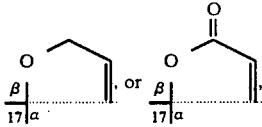

wherein $R^7$ is hydrogen or an alkanoyl residue of 1-4 carbon atoms,

U is hydrogen or an alkyl, hydroxy-alkyl, alkoxyalkyl, or alkanoyl-oxyalkyl group, each of 1-4 carbon atoms in each alkyl portion and alkanoyl portion;

$R^8$ is hydrogen, hydroxy, or an alkyl, O-alkyl, or O-alkanoyl group, each of 1-4 carbon atoms;

$R^9$ is hydrogen, hydroxy, or cyano or an O-alkyl or O-alkanoyl group of 1-4 carbon atoms;

$R^{10}$ is hydrogen or an alkyl or alkanoyl group of 1-10 carbon atoms;

m is 0, 1, 2, or 3; and k is 0, 1, or 2;

or a pharmacologically compatible acid addition salt thereof.

2. A compound of claim 1, wherein $R^2$ is $OR^3$.

3. A compound of claim 1, wherein X is keto.

4. A compound of claim 1, wherein A and B jointly are a further double bond between C4 and C5.

5. A compound of claim 1, wherein Z is a pentagonal ring residue.

6. A compound of claim 1, wherein $R^5$ and $R^6$ are, respectively, $OR^{10}$ and —H, and $R^{10}$ is H.

7. A compound of claim 1, wherein $R^5$ and $R^6$ are, respectively, $-OR^7$ and $-(CH_2)_m-CH_2-R^9$, wherein
$R^7$ is H,
m=0, and
$R^9$ is cyano or methoxy.

8. A compound of claim 1, wherein $R^5$ and $R^6$ are, respectively, $OR^7$ and $-C\equiv C-U$, wherein
$R^7$ is H and
U is methyl or hydroxymethyl.

9. A pharmaceutical composition comprising a compound of claim 1 and a pharmaceutically acceptable excipient.

10. A method of inducing antigestagenic effects, comprising administering an effective amount of a steroid of claim 1.

11. A method of inducing abortion, menstruation, or labor or of treating hormonal or hormone-dependent carcinomas, comprising administering an effective amount of a steroid of claim 1.

12. A method of treating disorders caused by an excess of glucocorticoids being present in the body, comprising administering an effective amount of a compound of claim 1.

13. A method of claim 12, wherein said disorder is glaucoma or a side effect of glucocorticoid therapy for treatment of a disease.

14. A method of claim 13, wherein the disease is Cushing's Syndrome, adipositas, arteriosclerosis, hypertension, osteoporosis, diabetes, or insomnia.

15. A $10\beta,11\beta$-bridged steroid of the Formula

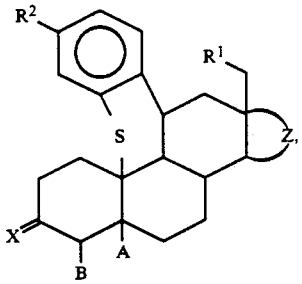

(I)

wherein
$R^1$ is H or methyl;
$R^2$ is H; cyano; an aliphatic group of up to 20 carbon atoms; an aliphatic group of up to 20 carbon atoms substituted by oxo; a $C_{4-7}$ cycloalkyl or $C_{4-7}$ cycloalkenyl group; an $OR^3-$, $SR^3-$, $-OSO_2-R^{11}$, or $NR^3R^4$-group; or a 4-cyano-, 4-methoxy- or 4-dimethylamino-substituted phenyl group;
$R^3$ is H or a $C_1-C_8$-alkyl residue,
$R^4$ is an $R^3$ group, cyano or a $C_1-C_{10}$-alkanoyl residue, or
$R^3$ and $R^4$ jointly with the inclusion of N is a 5- or 6-membered heterocyclic ring wherein the ring can additionally contain a further heteroatom N, O, or S;
$R^{11}$ is a perfluorinated $C_1-C_4$-alkyl group;

A and B either jointly are a further bond between C4 and C5, or A is an $\alpha$-hydroxy group and B is H;
X is a keto or oxime group; and
Z is a pentagonal or hexagonal ring residue of the formula

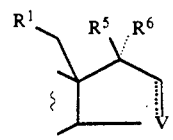

wherein
$R^1$ is H or methyl;
------ is a single or double bond;
V is $-CH_2-$, $-CH=$, $-CH_2CH_2-$, or $-CH_2-CH=$; and
$R^5$ and $R^6$ are, respectively,
$-OR^7$ and $-C\equiv C-U$,
$-OR^7$ and

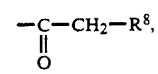

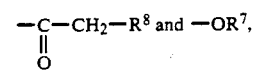

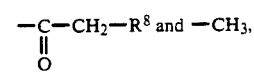

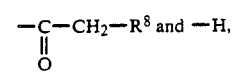

$-OR^7$ and $-(CH_2)_m-CH_2-R^9$,
$-OR^7$ and $-CH=CH(CH_2)_k-CH_2-R^9$,
$-OR^{10}$ and —H, or
$-OR^{10}/$ and $-(CH_2)_k-C\equiv C-E$, wherein E is halogen,

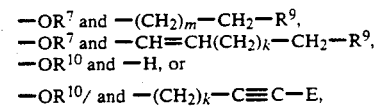

wherein
$R^7$ is hydrogen or an alkanoyl residue of 1–4 carbon atoms,
U is hydrogen or an alkyl, hydroxy-alkyl, alkoxyalkyl, or alkanoyl-oxyalkyl group, each of 1–4 carbon atoms in each alkyl portion and alkanoyl portion;
$R^8$ is hydrogen, hydroxy, or an alkyl, O-alkyl, or O-alkanoyl group, each of 1–4 carbon atoms;
$R^9$ is hydrogen, hydroxy, or cyano or an O-alkyl or O-alkanoyl group of 1–4 carbon atoms;
$R^{10}$ is hydrogen or an alkyl or alkanoyl group of 1–10 carbon atoms;
m is 0, 1, 2, or 3; and
k is 0, 1, or 2;
or a pharmacologically compatible acid addition salt thereof.

16. A compound of the Formula

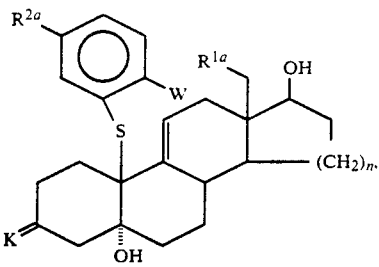

(II)

wherein $R^{1a}$ and $R^{2a}$ have the same meanings as $R^1$ and $R^2$, respectively, in Formula I wherein optionally hydroxy, mercapto, amino, oxo and/or terminal acetylene groups present in $R^{2a}$ are blocked, n is 1 or 2, K is a keto group blocked in the form of the ketal or thioketal, W is a bromine or iodine atom.

17. A 10β,11β-bridged steroid of the Formula

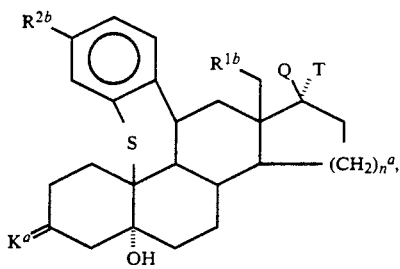

(III)

wherein $R^{1b}$, $R^{2b}$, $K^a$, and $N^a$ have the same meanings as $R^1$, $R^2$, K, and n of Formula I, respectively, but wherein optionally a hydroxy, mercapto, amino, oxo, and/or terminal acetylene group present in $R^{2b}$ is blocked, and Q is $R^5$ and T is $R^6$ and have the same means as $R^5$ and $R^6$ of Formula II, or Q and T jointly are a keto oxygen atom.

18. A compound of claim 17, wherein

Q is —$OR^{10}$, wherein $R^{10}$ is H, and T is —H.

19. (11α,17β)-9,11-Dihydro-17-hydroxy-7'-methoxy[1]benzothiopyrano[2',3',4':10,9,11]estra-4,9(11)-dien-3-one;

(11α,17β)-9,11-dihydro-17-hydroxy-7'-methoxy-17-(1-propynyl)[1]benzothiopyrano[2',3',4':10,9,11]estra-4,9(11)-dien-3-one;

[11,6α, 17β-(Z)]-9,11-dihydro-17-hydroxy-17-(3-hydroxy-1-propenyl)-7'-methoxy[1]benzothiopyrano[2',3',4',:10,9,11]estra-4,9(11)-dien-3-one;

(11α,17β)-7'-(diethylamino)-9,11-dihydroxy-17-hydroxy-17-(1-propynyl)[1]benzothiopyrano[2',3',4',10,9,11]estra-4,9(11)-dien-3-one;

(11α,17β)-9,11-dihydro-17-hydroxy-7'-(diethylamino)-17-(1-propynyl)[1]benzothiopyrano[2',3',4':10,9,1-1]estra-4,9(11)-dien-3-one;

(11α,17β)-9,11-dihydro-17-hydroxy-17-methoxymethyl-7'-(dimethylamino)[1 ]benzothiopyrano[2',3',4':10,9,11]estra-4,9(11)-dien-3-one;

(11α,17β)-9,11-dihydro-17-hydroxy-7'-(dimethylamino)-3-oxo[1]benzothiopyrano[2',3',4':10,9,1-1]estra-4,9(11)-dien-17-acetonitrile;

[11α,17β-(Z)]-9,11-dihydro-17-hydroxy-17-(3-hydroxy-1-propenyl)-7'-(dimethylamino)[1]benzothiopyrano[2',3',4':10,9,11]estra-4,9(11)-dien-3-one;

(11α,17β)-7'-acetyl-9,11-dihydro-17-hydroxy[1]benzothiopyrano[2',3',4':10,9,11]estra-4,9(11)-dien-3-one;

(11α,17β)-7'-acetyl-9,11-dihydro-17-hydroxy-17-(1-propynyl)[1]benzothiopyrano[2',3',4':10,9,11]estra-4,9(11)-dien-3-one;

(11α,17β)-7'-acetyl-9,11-dihydro-17-hydroxy-17-methoxymethyl[1]benzothiopyrano[2',3',4':10,9,1-1]estra-4,9(11)-dien-3-one;

(11α,17β)-7'-acetyl-9,11-dihydro-17-hydroxy-3-oxo[1]benzothiopyrano[2',3',4':10,9,11]estra-4,9(11)-dien-17-acetonitrile;

[11α,17β-(Z)]-7'-acetyl-9,11-dihydro-17-hydroxy-17-(3-hydroxy-1-propenyl)[1]benzothiopyrano[2',3',4':10,9,11]estra-4,9(11)-dien-3-one;

(11α,17β)-9,11-dihydro-17-hydroxy-7'-(isopropenyl)-17-methoxymethyl[1]benzothiopyrano[2',3',4':10,9,1-1]estra-4,9(11)-dien-3-one;

(11α,17β)-9,11-dihydro-17-hydroxy-7'-(isopropenyl)-3-oxo[1]benzothiopyrano[2',3',4':10,9,11]estra-4,9(11)-dien-17-acetonitrile;

[11α,17β-(Z)]-9,11-dihydro-17-hydroxy-17-(3-hydroxy-1-propenyl)[1]benzothiopyrano[2',3',4':10,9,11]estra-4,9(11)-dien-3-one;

(11α,17β)-9,11-dihydro-7'-ethynyl-17-hydroxy-17-(1-propynyl)[1]benzothiopyrano[2',3',4':10,9,11]estra-4,9(11)-dien-3-one; each a compound of claim 1.

20. A process for the production of compounds of Formula I

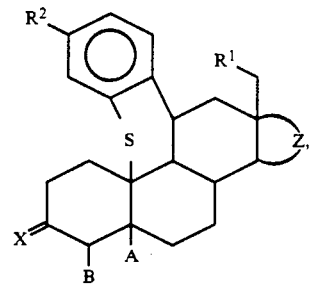

(I)

wherein the substituents $R^1$, $R^2$, X, A, B, and Z have the meanings indicated in Formula I, comprising cyclicizing compounds of Formula II

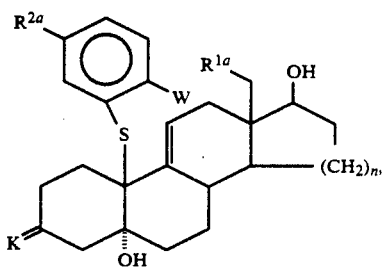

(II)

wherein $R^{1a}$ and $R^{2a}$ have the same meanings as $R^1$ and $R^2$, respectively, in Formula I, except that $OSO_2$—$R^{11}$, as well as n, K, and W have the meanings indicated in Formula I wherein any hydroxy, mercapto, amino, oxo, and/or terminal acetylene groups that may be presented are blocked, to the intermediate products of Formula IIIa

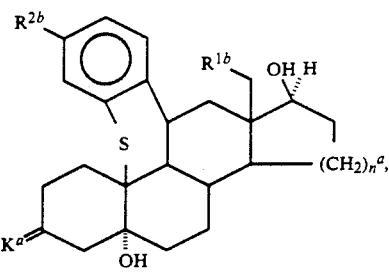

(IIIa)

wherein $R^{1b}$, $R^{2b}$, $K^a$, and $n^a$ have the same meanings as in Formula II,
and then, first, either (a) optionally, oxidizing the C-17 hydroxy group and subsequently, (b) if desired, freeing a hydroxy group on the phenylene ring, which exhibits a blocking group, of that blocking group; producing a corresponding perfluoroalkyl sulfonate, if desired, from the hydroxy compound; optionally, converting the perfluoroalkyl sulfonate, with a correspondingly substituted trialkyltin compound, into a compound which, optionally after further reactions, exhibits on the phenylene ring the desired substitution pattern, (c) functionalizing the D ring in the desired way according to conventional methods, subjecting the thus-obtained product, with formation of the 4(5)-double bond, to the effect of a dehydrating agent which is also capable of liberating the 3-oxo group and optionally further blocked groups, or (d) subjecting the thus-obtained product, with the formation of the 4(5)-double bond, to the effect of a dehydrating agent also capable of liberating the 3-oxo group and optionally further blocked groups and, subsequently, after blockage of the 3-oxo group, functionalizing the D-ring in the desired way, or the steps of (a) and (b) or (a) are executed after step (c) or (d), optionally freeing the thus-obtained product of blocking groups; if desired, alkylating or acylating the hydroxy, mercapto, and/or amino group that may be present on the phenylene ring; if desired, introducing a cyano residue into the phenylene ring and, optionally, reacting the thus-produced product with hydroxylamine hydrochloride to the compound of Formula I wherein X means the hydroxyamino group N OH; or producing a pharmaceutically acceptable acid additional salt thereof.

21. A process according to claim 20, comprising cyclizing the compounds of Formula II under reductively radical conditions to the intermediate products of Formula IIIa.

22. A process according to claim 20, comprising cyclizing the compounds of Formula II with tributyltin hydride in the presence of azobisisobutyronitrile.

23. A process according to claim 20, comprising converting the perfluoroalkyl sulfonate of step (b) with a correspondingly substituted trialkyltin compound, with the addition of a catalyst, into a compound having the desired substitution pattern on the phenyl ring, optionally after further reactions.

24. A process according to claim 23, comprising utilizing as the catalyst a transition metal compound.

25. A process according to claim 24, wherein the catalyst is a $Pd^0$ compound.

* * * * *

UNITED STATES PATENT AND TRADEMARK OFFICE
CERTIFICATE OF CORRECTION

PATENT NO.  : 5,093,507
DATED       : March 3, 1992
INVENTOR(S) : Cornelius SCHEIDGES et al.

It is certified that error appears in the above-identified patent and that said Letters Patent is hereby corrected as shown below:

Col. 25     Claim 15; line:1 - - - -

After Formula insert "(I)"

Col. 27     Claim 19; line: 7 - - - - -

After 11 delete " 60 "

Should read: - - -

$[11\alpha,17\beta-(Z)]$

Claim 19; line: 17 - - - -

Close Bracket ""1""

Signed and Sealed this

Eleventh Day of May, 1993

Attest:

MICHAEL K. KIRK

Attesting Officer

Acting Commissioner of Patents and Trademarks